US006576782B1

(12) United States Patent
Desmurs et al.

(10) Patent No.: US 6,576,782 B1
(45) Date of Patent: Jun. 10, 2003

(54) HALOGENATION OF PROTECTED PHENOLS IN META POSITION

(75) Inventors: Jean-Roger Desmurs, St-Symphorien d'Ozon (FR); Geneviève Padilla, Solaize (FR); Jean-Francis Spindler, Lyons (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/958,188

(22) PCT Filed: Apr. 5, 2000

(86) PCT No.: PCT/FR00/00851

§ 371 (c)(1),
(2), (4) Date: Oct. 4, 2001

(87) PCT Pub. No.: WO00/61523

PCT Pub. Date: Oct. 19, 2000

(30) Foreign Application Priority Data

Apr. 8, 1999 (FR) .............................................. 99 04399

(51) Int. Cl.⁷ .............................................. C07C 305/02
(52) U.S. Cl. .............................. 558/56; 558/54; 558/70; 560/129; 560/130; 564/218
(58) Field of Search .......................... 564/218; 560/129, 560/130; 558/54, 56, 70

(56) References Cited

U.S. PATENT DOCUMENTS

| 2,457,805 A | 1/1949 | Cade ........................... 260/479 |
| 2,508,334 A | 5/1950 | Moyle ......................... 260/479 |
| 3,416,911 A | 12/1968 | Hensel ........................... 71/71 |

FOREIGN PATENT DOCUMENTS

| FR | 1554976 | 1/1969 | |
| JP | 04 356438 | 12/1992 | ........... C07C/49/84 |

OTHER PUBLICATIONS

M. Boes: Novel Agonists of 5HT2c receptors . . . Journal of Medicinal Chemistry, vol. 40, No. 17, 15 Aout 1997 (Aug. 15, 1997), pp. 2762–2769 XP002124091.

M.H.Maguire: "Synthetic plant hormones, Part I. Some esters of phosphoric acid" Journal of the Chemical Society, 1953, pp. 1479–1482, XP002124092 Letchworth GB, p. 1480, composes nos. III and IV; p. 1481, 3$^{rd}$ paragraphe.

S. Sakakibara: The trifluoroacetate method of peptide synthesis . I—Bulletin of the Chemical Society of Japan, vol. 38, No. 11, 1965, pp. 1979–1984, XP002139154.

*Primary Examiner*—Shailendra Kumar

(57) ABSTRACT

The invention concerns a halogenation in position meta of a phenol fuction. Said halogenation comprises a step which consists in halogenating an aromatic derivative of a medium or advantageously strong acid, the aromatic radical being a phenyl substituted in ortho and in para by functions attracting electrons by inductive effect. The invention is applicable to organic synthesis.

19 Claims, No Drawings

HALOGENATION OF PROTECTED PHENOLS IN META POSITION

This application is an application under 35 U.S.C. Section 371 of International Application Number PCT/FR00/00851 filed on Apr. 5, 2000.

Synthetic process comprising a halogenation in the meta position of an aromatic acid derivative, intermediate compounds and use of the latter.

The present invention relates to a technique for the protection of phenols for the purpose of rendering selective a functionalization of the latter or at least of their backbone. A more particular subject matter of the invention is the protection of ortho- and para-substituted phenols so as to functionalize in the meta position, advantageously in the 5 position, of the phenyl backbone.

In the field of aromatic organic synthesis, one of the most acute problems is the selectivity of the functionalization of an aromatic nucleus and more specifically the regioselectivity of the functionalization of aromatic nuclei.

This problem becomes more acute when the functionalization takes place at an advanced stage in the synthesis. The more expensive the starting material in this functionalization stage, the more important it is to obtain selective reactions with a high yield.

This is in particular the case with trifunctionalized benzene nuclei which are to be functionalized a fourth time (that is to say, that it already comprises 3 substituents).

The problem is often complicated by the directing effect of some functional groups, in particular when these functional groups have a very marked directing effect, as is the case with phenol functional groups and their derivatives and aniline functional groups and their derivatives.

Thus, in Japanese Patent JPA 4356438, which relates to a general synthesis comprising a stage of halogenation of similar products to those which have just been mentioned above, the halogenation is carried out on the methyl ether of the phenol and a most indifferent yield is obtained since an isolated yield of less than 30% is obtained, which implies a doubtless very low selectivity (CY).

In addition, mention should be made, among the functionalizations which are the most difficult to carry out, of halogenations, which can be nonselective in several respects, first, with regard to the regio-selectivity and, secondly, with regard to the number of halogenations which the nucleus has to be subjected to.

This is why one of the aims of the present invention is to provide a process for the selective halogenation in the meta position of an aromatic derivative exhibiting an aniline functional group or a phenol functional group.

Another aim of the present invention is to provide a process of the above type in which the aromatic nucleus exhibits electron-withdrawing functional groups in the ortho position (in the 2 position) and in the para position (in the 4 position) (these electron-withdrawing functional groups advantageously being electron-withdrawing by an inductive effect; it is preferable for said electron-withdrawing functional groups to be electron-withdrawing by an inductive effect and advantageously electron donating by a mesomeric effect), whether these electron-withdrawing functional groups are alike or different.

Another aim of the present invention is to provide a protective system which promotes the above selectivity of halogenations.

Another aim of the present invention is to provide the use of molecule thus protected for the purpose of a selective halogenation.

Another aim of the present invention is to provide a process for the halogenation of the molecule thus protected for the purpose of a selective halogenation in the 5 position when the latter is distinct from the 3 position.

Another aim of the present invention is to provide a process of the above type which exhibits a selectivity (CY, that is to say conversion yield, namely the ratio of the amount of the desired product obtained to the amount of the starting substrate which has disappeared, everything being expressed in moles) at least to 80%, advantageously to 85%, preferably to 90%.

Another aim of the present invention is to provide a process of the above types which makes it possible to obtain a reaction yield (RY, that is to say the ratio of the amount of product obtained to the amount of starting substrate introduced) at least equal to 60%, advantageously to 70%, preferably to 80%.

Another aim of the present invention is to provide synthetic intermediate compounds.

These aims and others which will become apparent subsequently are achieved by means of an organic synthesis process comprising at least a stage of halogenation of the aromatic derivative of a moderate or advantageously strong acid in which the aromatic residue is a phenyl substituted in the ortho position and para position by functional groups which are electron-withdrawing by an inductive effect.

Thus, according to the present invention, it has been shown that the protection, by means of a strong acid and by means of a phenol or an aniline, played a role of induction in the meta and in particular in the 5 position of the derivatives of the above type.

This regioselectivity is particularly marked in the case of phenyl esters.

At least one (in particular that ortho to the protected phenol functional group), advantageously both electron-withdrawing functional groups, exhibit(s) an electron-donating property by mesomeric effect.

The most advantageous effects are obtained in the case where said electron-withdrawing functional groups, in any event at least one, preferably both, are halogen atoms.

In order to avoid side reactions, it is preferable for at least one if not both electron-withdrawing functional groups to be light halogens, that is to say chlorine or fluorine atoms.

The selectivity becomes increasingly advantageous in proportion as the starting materials become difficult to obtain. Thus, starting materials or the electron-withdrawing functional groups are respectively a chlorine and a fluorine are particularly well suited to the process of the present invention.

Mention may in particular be made of the compounds which exhibit a chlorine in the ortho position and a fluorine in the para position.

As regards said strong or moderate acids, it is preferable for said strong or moderate acid to be chosen from oxygen-comprising acids.

It is also desirable for said strong or moderate acid to exhibit a $pK_a$ of less than or equal to 4, advantageously of less than or equal to 2, preferably of less than or equal to 0.

The easiest acids to use are those which can be chosen from the following list: acids or acid esters of phosphoric (ortho-, pyro- or poly-) or phosphonic acids, indeed even phosphinic, sulfonic and alpha-polyhalocarboxylic acids.

A specific mention must be made of sulphonic acids, which are particularly well suited to the present invention. Thus, use may be made either of arylsulfonic acids, the outstanding examples of which are benzenesulfonic and para-toluenesulfonic acids; use may also be made of alkylsulfonic acids, the outstanding example of which is methanesulfonic acid, more often known as mesylic acid. The latter acid exhibits a not insignificant hydrophilicity, which can sometimes be an advantage and sometimes a disadvantage. When more lipophilic acids are desired, it is advisable to turn toward acids either comprising more than 5 carbon atoms or fluorinated acids, as will be seen below. If more hydrophilic acids are desired, it is possible to turn toward polyacids, such as phosphoric or phosphonic acids; polyhalocarboxylic acids are to be ranked among compounds with a lipophilic tendency (this lipophilicity means good solubility in the organic phases).

A specific mention must be made of sulfonic acids fluorinated on the alpha position and, if appropriate, beta position. Mention may thus be made of trifluoromethylsulfonic acid or trifluoric acid. However, it should be emphasized that perfluorosulfonic acids are particularly fat-soluble acids, which makes possible good solubility in water-imiscible organic phases.

This solubility in organic phases can constitute an advantage or else a disadvantage, depending upon the situation and according to whether it is or is not desired to separate the final product by recovering it in an organic phase.

The halogenation is advantageously carried out in a known way by using techniques which employ halogens which are described as being cationic.

This halogenation can be a chlorination or a bromination. In the latter case, a particularly advantageous reactant is the compound of formula BrCl, which can be introduced directly into the medium or can be synthesized in situ.

As regards the solvents and the other components of the reaction medium, it should be pointed out that it is preferable for there to be, in the reaction medium, at least as many acid functional groups as esterified phenol functional groups in the substrate.

These acids are preferably protic acids, or Bronsted acids, and in particular moderate or strong acids, that is to say acids for which the $pK_a$ is at least equal to that of carboxylic acids (that is to say, approximately 4). It is preferable to have used strong acids, such as sulfuric acid or any other acid of similar acidity ($pK_a$ less than or equal to 2, preferably less than or equal to 0).

To provide for the cationic nature of halogenation, it is preferable to carry out the halogenation in the presence of a catalyst for the cationic dissociation of the halogenating agents, more particularly of Lewis acid. These Lewis acids are advantageously present at a level of 1/1000 to 10 mol %, preferably of 1 to 5 mol %, with respect to the substrate to be halogenated.

The preferred Lewis acids are metals, the salts of which are well dissociated in a sulfuric acid medium, and more particularly trivalent metals. Mention may in particular be made of aluminum ($Al^{+++}$) and especially ferric iron.

The presence of acids as solvents or simply present in the medium at an amount at least equal to 1 times the number of phenol functional groups, advantageously 1.5 times (generally and preferably there is only a single phenol functional group and thus the amount of acids present and acting as solvents is thus at least equal to 1 times the molar amount of substrates, indeed even at least equal to 1.5 times the amount of substrates), has a tendency to reduce the reactivity of the substrates toward the halogenation reactants. It is consequently desirable to heat the reaction medium to a temperature at least equal to 30° C. Generally, it is unnecessary to heat above 100° C.

The preferred substrates are compounds of formula 1 below in which Y is hydrogen, the halogenation then being carried out in the 5 position.

Another aim of the present invention is to provide, as intermediate compounds, compounds of formula 1:

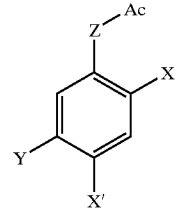

Formula 1 where Ac represents a residue such that AcOH is an oxygen-comprising acid with a $pK_a$ of less than or equal to 2, advantageously of less than or equal to 1, preferably of less than or equal to 0;

where X and X', which are alike and/or different, represent a halogen, advantageously a chlorine and/or a fluorine;

where Y represents a hydrogen atom or a chlorine, bromine or iodine atom;

where Z represents either an —NR— group or a chalcogen, preferably oxygen or sulfur, more preferably oxygen;

where R represents an acyl group lato sensu, that is to say the residue of an oxygen-comprising acid after removal of an OH group; R can also be a hydrogen atom. It should be pointed out that R can be connected to the Ac group, so as to form a cyclic imide group with the nitrogen atom. This group can comprise residues of carboxylic acid functional group to form cyclic imides, or else mixed carboxylic or sulfonic ones, or any pair composed of two alike or different components capable of forming, by ring, an imide or an imide equivalent.

Thus, the present invention is targeted at the use of mono- or polyacids for protecting an amine functional group or more preferably a phenol functional group, so as to promote a halogenation, which can be a chlorination, a bromination or an iodination, in the meta position, advantageously in the 5 position, with respect to said aniline or phenol functional group.

Although they give good results and although they are easy to synthesize, the intermediate compounds which are both carbonaceous and not very carbonaceous, while being nonfluorinated, are the least advantageous.

It is thus preferable to use, as intermediate compounds, either those which do not exhibit a carbon atom, or those which have at least 3, preferably at least 5, carbons, or, finally, those which are halogenated, preferably fluorinated.

The following nonlimiting examples illustrate the invention.

EXAMPLE 1

Protection of the Phenol

Synthesis of 2-chloro-4-fluorophenyl methanesulfonate 34.32 g of 2-chloro-4-fluorophenol (0.201 mol), 80 g of dichloromethane, 41.46 g of potassium carbonate (0.300 mol) and 25.19 g of mesyl chloride (0.218 mol) are charged to a 150 ml reactor.

The reaction mixture is left stirring for 3 hours. The organic phase is recovered after filtering off the salts. The dichloromethane solution is subsequently washed successively with 100 ml of potassium carbonate solution at pH=8, 100 ml of 20% (weight/weight) potassium hydrogencarbonate solution and then 100 ml of water.

After removing the dichloromethane, the crude product is purified by recrystallization from an MeOH/water (70/30 w/w) mixture.

The isolated product exhibits an assay of greater than 98% and the 2-chloro-4-fluorophenyl methanesulfonate yield is equal to 65%.

Synthesis of 2-chloro-4-flurophenyl acetate 34.32 g of 2-chloro-4-fluorophenol (0.201 mol), 80 g of dichloromethane, 41.46 g of potassium carbonate (0.300 mol) and 17.78 g of acetyl chloride (0.218 mol) are charged to a 150 ml reactor.

The reaction mixture is left stirring for 3 hours. The organic phase is recovered after filtering off the salts. The dichloromethane solution is subsequently washed successively with 100 ml of potassium carbonate solution at pH=8, 100 ml of 20% (weight/weight) potassium hydrogencarbonate solution and then 100 ml of water.

The 2-chloro-4-fluorophenyl acetate is recovered crude after removing the dichloromethane and excess acetyl chloride.

The isolated yield of 2-chloro-4-fluorophenyl acetate is 84% and the assay is 95% by weight.

EXAMPLE 2

Bromination of the Protected Phenol

Synthesis of 5-bromo-2-chloro-4-fluorophenyl methanesulfonate 100 ml of 96% sulfuric acid, 0.1 g of iron powder (0.0018 mol), 2.04 g of 2-choro-4-fluorophenyl methanesulfonate (0.0091 mol) and 3.14 g of bromine (0.019 mol) are charged to a 150 ml reactor.

The reaction mixture is then heated to 50° C. and chlorine (1.35 g, 0.019 mol) is added over a period of one hour.

At the end of the reaction, the sulfuric acid solution is raised with nitrogen and then it is poured into 250 ml of ice-cold water. The crude 5-bromo-2-chloro-4-fluorophenyl methanesulfonate is extracted from the sulfuric acid solution with dichloromethane (3×50 ml).

The dichloromethane solution is subsequently washed with water until a pH equal to 5 is achieved. The crude 5-bromo-2-chloro-4-fluoro-phenyl methanesulfonate is collected after distilling off the dichloromethane and drying. The isolated yield is 90% and the purity of the crude product is 92% by weight.

Synthesis of tris(5-bromo-2-chloro-4-fluorophenyl) phosphate 100 ml of 96% sulfuric acid, 0.1 g of iron powder (0.0018 mol), 2.0 g of tris(2-chloro-4-fluoro-phenyl)phosphate (0.00373 mol) and 3.14 g of bromine (0.019 mol) are charged to a 150 ml reactor.

The reaction mixture is then heated to 50° C. and chlorine (1.35 g, 0.019 mol) is added over a period of one hour.

At the end of the reaction, the sulfuric acid solution is stripped with nitrogen and then it is poured into 250 ml of ice-cold water. The crude methane tris(5-bromo-2-chloro-4-fluorophenyl)phosphate is extracted from the sulfuric acid solution with dichloromethane (4×50 ml). The dichloromethane solution is subsequently washed with water until a pH equal to 5 is achieved. The crude tris(5-bromo-2-chloro-4-fluorophenyl)phosphate is collected after distilling off the dichloromethane and drying. The isolated yield is 83% and the purity of the crude product is 94% by weight.

EXAMPLE 3

Chlorination of the Protected Phenol Synthesis of 2,5-dichloro-4-fluorophenyl methanesulfonate 100 ml of 96% sulfuric acid, 0.1 g [lacuna] and 2.04 g of 2-chloro-4-fluorophenyl methanesulfonate (0.0091 mol) are charged to a 150 ml reactor.

The reaction mixture is then heated to 30° C. and chlorine (1.35 g, 0.019 mol) is added for a period of one hour.

At the end of the reaction, the sulfuric acid solution is stripped with nitrogen and then it is poured into 250 ml of ice-cold water. The crude 2,5-dichloro-4-fluorophenyl methanesulfonate is extracted from the sulfuric acid solution with dichloromethane (3×50 ml).

The dichloromethane solution is subsequently washed with water until a pH equal to 5 is achieved. The crude 2,5-dichloro-4-fluorophenyl methanesulfonate is collected after distilling off the dichloromethane and drying.

The isolated yield is 93% and the purity of the crude product is 91 weight %.

Synthesis of (2,5-dichloro-4-fluorophenyl)acetate 100 ml of acetic acid and 2.0 g of (2-chloro-4-fluorophenyl)acetate (0.0106 mol) are charged to a 150 ml reactor.

The reaction mixture is then heated to 50° C. and chlorine (1.35 g, 0.019 mol) is added over a period of one hour.

At the end of the reaction, the acetic acid solution is stripped with nitrogen and then it is poured into 250 ml of ice-cold water. The crude (2,5-dichloro-4-fluorophenyl)acetate is extracted from the aqueous solution with dichloromethane (4×50 ml).

The dichloromethane solution is subsequently washed with water until a pH equal to 5 is achieved. The crude (2,5-dichloro-4-fluorophenyl)acetate is collected after distilling off the dichloromethane and the acetic acid.

The isolated yield is 85% and the purity of the crude product is 89 weight %.

EXAMPLE 4

Deprotection of the Phenol After Halogenation

Synthesis of 5-bromo-2-chloro-4-fluorophenol 2 g of 5-bromo-2-chloro-4-fluorophenyl methanesulfonate (0.0066 mol), 32 ml of ethanol and 8 g of 10 weight % aqueous potassium hydroxide (0.0145 mol) are charged to a 150 ml reactor.

The reaction mixture is subsequently left stirring at ambient temperature for 3 hours.

At the end of the reaction, the reaction medium is acidified to pH=1 with 1N hydrochloric acid. The crude 5-bromo-2-chloro-4-fluorophenol is extracted from the aqueous solution with dichloromethane (3×5 ml).

The dichloromethane solution is subsequently washed with water until a pH equal to 3 is achieved. The crude product is collected after distilling off dichloromethane and ethanol.

The isolated yield is 89% and the purity of the crude product is 95 weight %.

What is claimed is:

1. An organic synthesis process, comprising the step of halogenating at a temperature at least equal to 30° C. in the presence of a catalytic cationic dissociating amount of a Lewis acid, an aromatic derivative of a moderate or strong acid, comprising an acid group and an aromatic group, said aromatic group being a phenyl group substituted in the ortho position and in the para position by functional groups which are electron-withdrawing by an inductive effect.

2. The process according to claim 1, wherein said derivative is an anilide or a phenyl ester.

3. The process according to claim 1, wherein one or two of the electron-withdrawing functional groups are electron-donating group by mesomeric effect.

4. The process according to claim 1, wherein one or two of the electron-withdrawing functional groups are halogen atoms.

5. The process according to claim 1, wherein one or two of the electron-withdrawing functional groups are selected from the groups consisting of fluorine atom, and chlorine atom.

6. The process according to claim 1, wherein one of the electron-withdrawing functional groups is a chlorine atom, and one one of the electron-withdrawing functional groups is a fluorine atom.

7. The process according to claim 6, wherein the chlorine atom in ortho position, and the fluorine atom is in para position.

8. The process according to claim 1, wherein the acid group comprises an oxygen atom.

9. The process according to claim 1, wherein the acid group has a $pK_a$ of less than or equal to 4.

10. The process according to claim 9, wherein the acid group has a $pK_a$ of less than or equal to 2.

11. The process according to claim 10, wherein the acid group has a $pK_a$ of less than or equal to 0.

12. The process according to claim 1, wherein the acid group is selected from the group consisting of phosphoric acids groups, acid esters groups thereof, phosphonic acids groups, acid esters groups thereof, sulfonic acids groups, acid esters groups thereof, carboxylic acids groups which are alpha-polyhalogenated, and acid esters groups thereof.

13. The process according to claim 12, the acid group is a sulfonic acid group selected from the group consisting of alkylsulfonic acid groups, arylsulfonic acid groups, perfluoroalkylsulfonic acid groups.

14. The process according to claim 1, wherein halogenating is carried out in position 5.

15. The process according to claim 1, wherein halogenating is chlorinating or brominating.

16. The process according to claim 1, wherein halogenating is carried out by using a cationic reactant.

17. The process according to claim 1, wherein halogenating is brominating, and is carried out by using BrCl.

18. The process according to claim 17, wherein BrCl is introduced directly or prepared in situ.

19. The process according to claim 1, wherein the amount of the Lewis acid is present at a level of 1/1000 to 10 moles % with respect to the aromatic derivative to be halogenated.

* * * * *